(12) United States Patent
Heidmann et al.

(10) Patent No.: US 10,946,149 B2
(45) Date of Patent: Mar. 16, 2021

(54) APPARATUS FOR SUPPLYING A BREATHING GAS

(71) Applicant: ResMed Pty Ltd, Bella Vista (AU)

(72) Inventors: Dieter Heidmann, Geretsried (DE);
Klaus Henry Schindhelm, Sydney (AU); Knut Jöchle, Schondorf (DE)

(73) Assignee: ResMed Pty Ltd, Bella Vista (AU)

( * ) Notice: Subject to any disclaimer, the term of this patent is extended or adjusted under 35 U.S.C. 154(b) by 167 days.

(21) Appl. No.: 15/970,189

(22) Filed: May 3, 2018

(65) Prior Publication Data

US 2018/0311453 A1 Nov. 1, 2018

Related U.S. Application Data

(63) Continuation of application No. 14/461,692, filed on Aug. 18, 2014, now Pat. No. 9,981,094, which is a continuation of application No. 11/480,568, filed on Jul. 5, 2006, now Pat. No. 8,839,786.

(30) Foreign Application Priority Data

Jul. 5, 2005 (DE) .................. 10 2005 031 388.4

(51) Int. Cl.
*A61M 16/00* (2006.01)
*A61M 16/10* (2006.01)

(52) U.S. Cl.
CPC .... *A61M 16/0003* (2014.02); *A61M 16/0057* (2013.01); *A61M 16/0066* (2013.01); *A61M 16/107* (2014.02); *A61M 2205/42* (2013.01)

(58) Field of Classification Search
CPC .......... A61M 16/0003; A61M 16/0057; A61M 16/107; A61M 16/0066; A61M 2205/42
See application file for complete search history.

(56) References Cited

U.S. PATENT DOCUMENTS

| | | |
|---|---|---|
| 3,874,023 A | 4/1975 | Tschudy |
| 4,160,517 A | 7/1979 | Buisker |
| 4,767,285 A | 8/1988 | Jyoraku et al. |
| 4,927,119 A | 5/1990 | Frost |
| 4,978,281 A * | 12/1990 | Conger, IV ........... F04D 25/082 264/271.1 |
| 5,127,622 A | 7/1992 | Whelpley |

(Continued)

FOREIGN PATENT DOCUMENTS

| | | |
|---|---|---|
| EP | 0295455 | 9/1992 |
| WO | WO 1999/000601 | 1/1999 |

(Continued)

OTHER PUBLICATIONS

U.S. Appl. No. 10/533,840 (2006/0033681), filed May 2005 (Feb. 2006), Hashimoto et al.

(Continued)

*Primary Examiner* — Kendra D Carter
*Assistant Examiner* — Jonathan S Paciorek
(74) *Attorney, Agent, or Firm* — Nixon & Vanderhye P.C.

(57) ABSTRACT

An apparatus for supplying a breathing gas at a pressure level that at least in some phases is above ambient pressure includes a blower device including an impeller and a housing device to receive the impeller. A suspension device is structured to support the blower device. The suspension device includes a variable suspension characteristic.

12 Claims, 6 Drawing Sheets

(56) References Cited

U.S. PATENT DOCUMENTS

| | | | |
|---|---|---|---|
| 5,307,529 A | * | 5/1994 | Wang ................ A61H 33/025 4/541.5 |
| 5,364,086 A | | 11/1994 | Paton |
| 5,567,127 A | * | 10/1996 | Wentz .................... A47L 7/00 415/119 |
| 5,704,345 A | | 1/1998 | Berthon-Jones et al. |
| 5,893,705 A | | 4/1999 | Khan et al. |
| 6,076,580 A | * | 6/2000 | Mazhar .................. B60C 5/24 152/333.1 |
| 6,216,691 B1 | | 4/2001 | Kenyon et al. |
| 6,287,095 B1 | * | 9/2001 | Saputo ................ A47C 27/081 417/472 |
| 6,315,526 B1 | * | 11/2001 | Jones .................. F04D 29/601 417/363 |
| 6,397,841 B1 | | 6/2002 | Kenyon |
| 6,565,334 B1 | | 5/2003 | Bradbury et al. |
| 6,910,483 B2 | | 6/2005 | Daly et al. |
| 8,393,320 B2 | | 3/2013 | Kenyon |
| 2001/0014290 A1 | | 8/2001 | Takura et al. |
| 2003/0168064 A1 | * | 9/2003 | Daly .................. F04D 17/164 128/204.18 |
| 2007/0007271 A1 | | 1/2007 | Heidmann et al. |
| 2014/0352696 A1 | | 12/2014 | Heidmann et al. |

FOREIGN PATENT DOCUMENTS

| | | |
|---|---|---|
| WO | WO 2000/038771 | 7/2000 |
| WO | WO 2004/108198 | 12/2004 |
| WO | WO 2004/112873 | 12/2004 |

OTHER PUBLICATIONS

U.S. Appl. No. 10/864,869 (2005/0103339), filed Jun. 2004 (May 2005), Daly et al.

International Search Report for PCT/AU2006/001616, dated Dec. 21, 2006.

International Search Report for PCT/AU2006/001617, dated Dec. 21, 2006.

U.S. Appl. No. 12/083,350, filed Apr. 10, 2008.

U.S. Appl. No. 12/083,937, filed Apr. 22, 2008.

Office Action issued in corresponding German Appln. No. 10 2005 031 388.4 dated Feb. 2, 2015, with English translation thereof.

* cited by examiner

Fig.1a
(Prior Art)
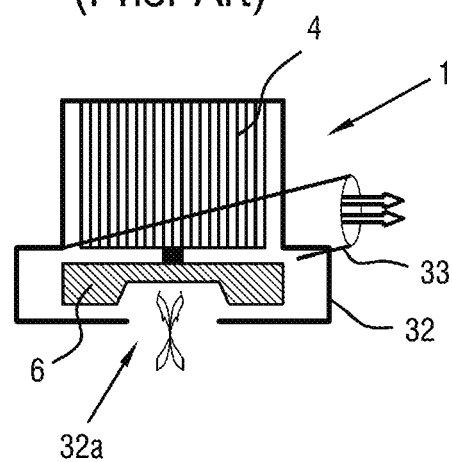
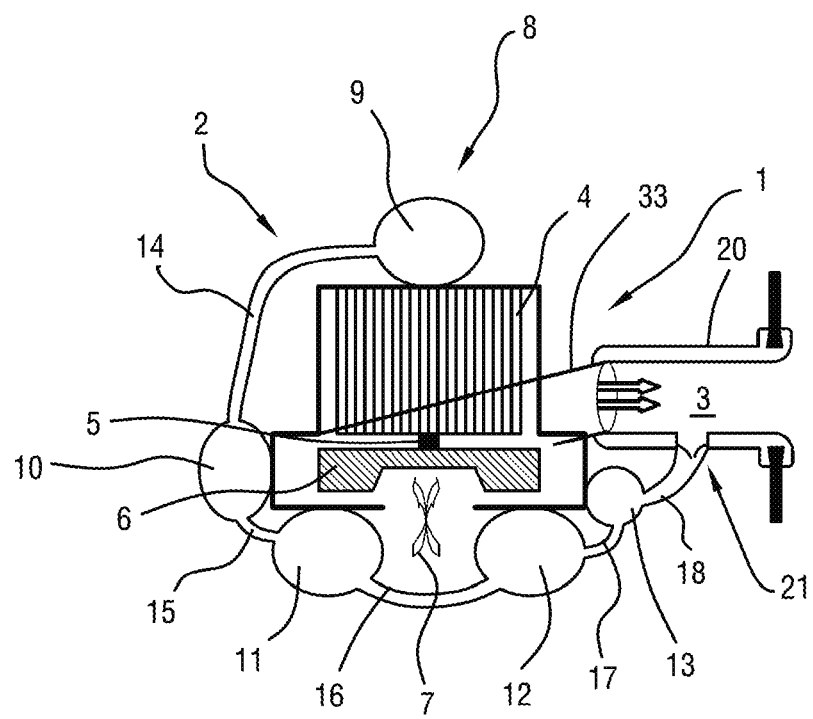
Fig. 1b

Fig. 5
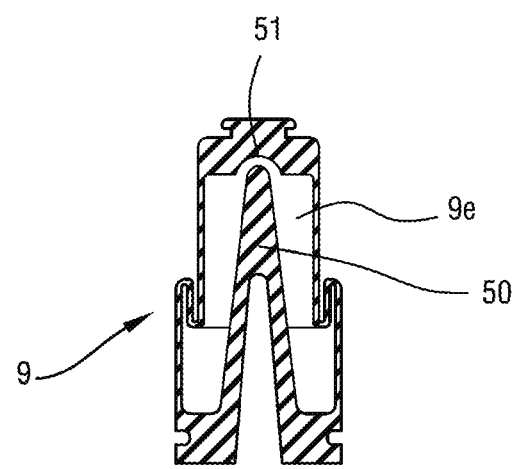
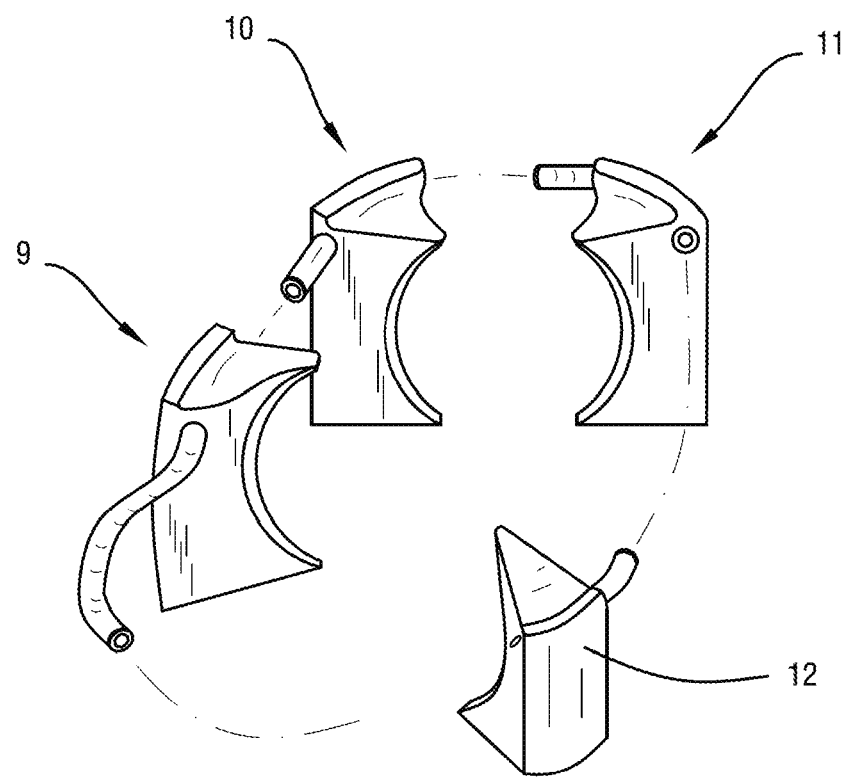
Fig. 6a

Fig. 6b
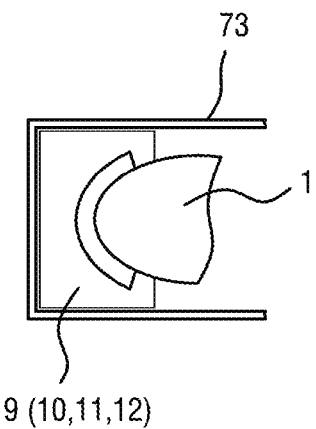
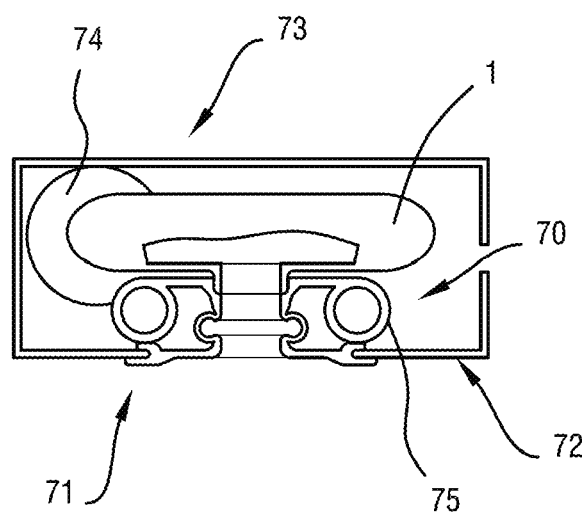
Fig. 7

APPARATUS FOR SUPPLYING A BREATHING GAS

CROSS-REFERENCE TO RELATED APPLICATIONS

This application is a continuation of U.S. application Ser. No. 14/461,692, filed Aug. 18, 2014, allowed, which is a continuation of U.S. patent application Ser. No. 11/480,568, filed Jul. 5, 2006, now U.S. Pat. No. 8,839,786, which claims the benefit of German Application No. 10 2005 031 388.4, filed Jul. 5, 2005, which is incorporated herein by reference in its entirety.

FIELD OF THE INVENTION

The present invention relates to an apparatus for supplying a breathing gas, e.g., ambient air, at a pressure level that at least in some phases is above ambient pressure. The invention also relates to an apparatus for therapy and/or diagnosis of sleep-related respiratory disturbances by bringing about a pneumatic splinting effect in the region of the upper respiratory passages. Such apparatuses may be in the form of CPAP devices for home use.

BACKGROUND OF THE INVENTION

In known CPAP devices, breathing gas supplied to a user is typically delivered by a supply device at a pressure level that is above ambient pressure. This supply device may be embodied as a blower device, with a motor-driven impeller in the form of an axial, half-axial, or radial impeller. The supply device forms a pressure gate per se, by which a portion toward the patient of an air-carrying system is made to be at a higher pressure level than a portion of the air-carrying system on the suction side that is open toward the environment. Carrying the breathing gas from this supply device to a user can be done via line segments internal to the device, an air humidifier, a flexible hose line, and a breathing mask device connected to the hose. To achieve a high degree of comfort during therapy, CPAP devices are typically embodied such that they cause as little operating noise as possible. To reduce the operating noise, it is possible to provide sound-absorbing insulating materials in the interior of the CPAP, for absorbing any acoustic events that are introduced into the breathing gas tract by the supply device.

SUMMARY OF THE INVENTION

One aspect of the invention relates to an apparatus for supplying a breathable gas at a pressure level that at least in phases is above ambient pressure, wherein the apparatus includes very quiet operation and offers advantages in terms of production, maintenance, and/or operation.

Another aspect of the invention relates to an apparatus for supplying a breathing gas at a pressure level that at least in some phases is above ambient pressure. The apparatus includes a blower device including an impeller and a housing device to receive the impeller. A suspension device is structured to support the blower device. The suspension device includes a variable suspension characteristic.

As a result, a breathing gas delivery device, in particular a CPAP device, may be provided in which the propagation of any noise phenomena generated or caused by the blower device, both via the breathing gas tract system and via the device structure, is reduced in a way that is especially effective compared to previous constructions. Especially advantageously, it becomes possible to reduce the secondary noise component, that is, the noise component not introduced directly through the blower but rather via the further device structures into the breathing gas tract system. The variable suspension characteristic may be embodied using one or more elastomer structures.

In another embodiment of the invention, the suspension device may be structured such that the suspension characteristic may be variable in terms of the suspension rigidity. The suspension rigidity, in an embodiment of the invention, may be varied as a function of certain device operation parameters, e.g., the breathing gas pressure. The suspension device may be structured such that the suspension rigidity, or the support forces that support the blower device, likewise increase with increasing breathing gas pressure. As an alternative, or in combination with this provision, the overall suspension device may be structured such that the suspension characteristic, e.g., its support rigidity, may be variable in accordance with the power demand of the blower device or in accordance with a blower reaction moment. This arrangement allows the blower device to be suspended in such a way that each of the suspension forces is only at or near the level for sufficiently secure support of the blower device. As a result, because of the only slight suspension rigidity, the propagation of structure-home sound events from the blower device into the corresponding device or its surroundings may be averted and/or reduced.

In another embodiment of the invention, the suspension device may be structured such that the rigidity of the suspension increases with the breathing gas pressure. As an alternative to this provision, or in combination with it, the suspension device may be structured such that the suspension rigidity is variable in accordance with the power demand of the blower device. In an embodiment, the suspension rigidity may be temporarily increased in phases of major acceleration and/or deceleration of the blower device.

In an embodiment, the rigidity of the suspension device may be adjusted in accordance with the blower reaction moment. This blower reaction moment may be ascertained from the instantaneous power demand of a motor device, provided for driving the blower impeller, or may be detected by detection devices.

In another embodiment of the invention, the suspension device may be structured as an air chamber structure. The air chamber structure may include one or more chambers, e.g., balloon, annular hose, segmental or cylindrical chambers, that function as support chambers. By the effect of the intrinsic strength of the chamber wall and under the effect of the air pressure prevailing in the support chambers, the support chambers support the blower device, including the blower motor, adequately well in a receiving chamber adapted to receive the blower device.

The support chambers may be structured and disposed to provide a suspension system, e.g., a tripod system, which supports the blower device with a predetermined minimum rigidity or minimum supporting force.

One or more stop devices may be provided that assure a minimum suspension effect for sufficiently supporting the blower device in the receiving chamber provided for receiving the blower device. These stop devices may form an integral component of the elastomer walls that are intended to form the support chambers.

The geometry of the support chambers, and in particular the geometry of their walls and the geometry of the portions that contact the blower device, may be adapted such that as a result, the least possible input and transfer of structure-borne sound takes place.

In embodiments of the invention, the support chambers may be coupled to one another via line segments and can thus communicate with one another. At least one of these line segments may be coupled to the portion of the breathing gas supply system on the compression side and serves here to subject the support chamber system to pressure.

In an embodiment, the delivery of air to the support chamber system, and in particular the diversion of the air from the region on the compression side of the breathing gas tract system, may incorporate a one-way valve or a check valve device, thus avoiding a reverse flow of the initially diverted air from the support chamber system into the breathing gas tract system. Also, a throttle device, e.g., porous plugs of sintered material, may be provided to enable a defined outflow of the air from the support chamber system and to the environment, so that via this outflow, pressure suppression may be provided.

In another embodiment of the invention, the support chamber system may carry air in such a way that a stream of cooling air is created, making it possible to divert the waste heat produced by the motor via the air stream flowing via the support chamber system. To that end, at least one of the support chambers, or at least one chamber communicating with the support chamber system, may be structured such that it is defined in at least some portions by a wall of the motor that functions as a heat dissipation wall.

Another aspect of the invention relates to an apparatus for supplying a breathing gas at a pressure level that at least in some phases is above ambient pressure. The apparatus includes a blower device including an impeller and a housing device to receive the impeller. A suspension device is structured to elastically and resiliently support the blower device. The suspension device includes suspension structures structured as air chambers.

Another aspect of the invention relates to an apparatus for supplying a breathing gas at a pressure level that at least in some phases is above ambient pressure. The apparatus includes a blower device including an impeller and a housing device to receive the impeller. A cassette-like housing insert is structured to receive the blower device. The cassette-like housing insert includes an air spring system that elastically and resiliently suspends the blower device.

Another aspect of the invention relates to an apparatus for supplying a breathing gas at a pressure level that at least in some phases is above ambient pressure. The apparatus includes a blower device including an impeller and a housing device to receive the impeller. A suspension device is structured to elastically and resiliently support the blower device. The suspension device includes an elastomer diaphragm structure.

Another aspect of the invention relates to an apparatus for supplying a breathing gas at a pressure level that at least in some phases is above ambient pressure. The apparatus includes a blower device including an impeller and a housing device to receive the impeller. A suspension device is structured to elastically and resiliently support the blower device. The suspension device is formed by an elastomer line structure, and the elastomer line structure includes air chambers that effect an air-cushioned support of the blower device.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 1a is a sketch that illustrates a blower device for supplying a breathing gas to a pressure level that is above ambient pressure, particularly for a therapy and/or diagnosis device intended for administering a breathable gas;

FIG. 1b is a schematic view illustrating an apparatus according to an embodiment of the invention, with an air cushion suspension device for suspending a blower device of FIG. 1a;

FIG. 2 is a schematic view of an apparatus according to another embodiment of the invention, with an additional elastomer sound damper device integrated into a receiving chamber intended for receiving the blower device of FIG. 1a;

FIG. 5 is a cross-sectional view of a support chamber device with an integrated end stop structure according to an embodiment of the present invention;

FIG. 6a is a perspective view of a segmental suspension device according to an embodiment of the invention, including support chambers, for a blower device;

FIG. 6b is a sketch that illustrates the arrangement of the segments of FIG. 6a inside a receiving portion intended for receiving a blower;

FIG. 7 is a sketch that illustrates an elastomer structure for the sealed-off attachment of an intake line segment of a blower device according to an embodiment of the invention;

DETAILED DESCRIPTION OF ILLUSTRATED EMBODIMENTS

Figure 2:
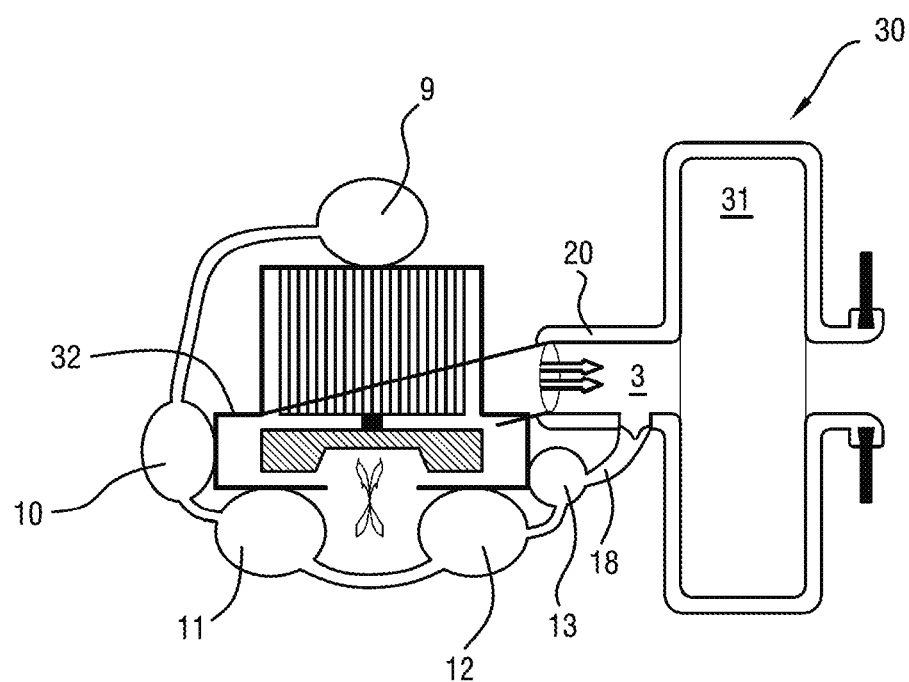

FIG. 1a shows a blower device 1, known per se, for a CPAP device. Blower device 1 includes a motor 4, an impeller 6 driven by the motor, and a housing device 32 structured to receive the impeller 6. The housing device 32 is provided with a pressure stub or tube 33 for carrying the breathing gas, supplied by the impeller 6, onward to a system portion on the compression side of a CPAP device. The impeller housing 32 also forms an intake portion 32a, by which entry of the air to be pressurized/aspirated by the impeller 6 takes place. Pressurization/aspiration may take place in phases. Blower device 1 is suspended via the suspension device shown in FIG. 1b, elastically, resiliently and acoustically largely insulated, in a corresponding interior of a CPAP device.

As shown in FIG. 1b, the blower device 1 is received in a cassette-like receiving portion 2 and serves to supply a breathable gas, e.g., ambient air, into a portion 3 on the compression side of a CPAP device.

The blower device 1, as already noted in conjunction with FIG. 1*a*, includes an electric motor 4 and an impeller 6 coupled to a drive shaft 5 of the electric motor 4. By means of this impeller 6, air 7, flowing in from the environment via inflow devices (not shown here), is supplied at a pressure level into the portion 3 on the compression side. The blower device 1 is elastically, resiliently suspended and supported in the receiving portion 2 by a suspension device 8.

The suspension device 8 is structured such that its suspension characteristic is variable. In the illustrated embodiment, the rigidity of the suspension device increases with an increase in the breathing gas pressure provided to the portion 3 on the compression side. In the illustrated embodiment, this arrangement may be attained by providing the suspension device 8 with one or more elastically deformable support chambers 9, 10, 11, 12, 13, e.g., balloon-like structures. The support chambers 9, 10, 11, 12, 13 communicate with one another via line devices 14, 15, 16, 17, which are embodied here as hose-like structures. Overall, in the illustrated embodiment, the suspension device 8 is structured as an integral hollow chamber structure made from an elastomer material. This hollow chamber structure is coupled to the portion 3 of a breathing gas tract system on the compression side, via a further line segment 18, e.g., hose-like structure.

The suspension device 8 may be structured by suitably defining and dimensioning the geometry of the chamber wall of the support chambers 9, 10, 11, 12, 13 to define a suspension system that assures a requisite minimum support of the blower device 1 and furthermore brings about effective acoustic decoupling within the relevant excitation spectrum. It is also possible to provide structures in the receiving portion 2, which provide adequate pre-positioning of the blower device. Typical positioning of the blower device for operation is then effected only after suitable inflation of one or more of the support chambers 9, 10, 11, 12, 13. In the region of the receiving portion 2, bearing portions may be provided, which provide adequate pre-positioning and securing of the individual support chambers 9, 10, 11, 12, 13.

The coupling of the blower device 1 to the breathing gas tract system on the compression side of the CPAP device may be effected via an elastomer stub or tube 20. In an embodiment, the elastomer stub 20 may be integrally formed with the support chambers 9, 10, 11, 12, 13, or with the line segments 14, 15, 16, 17, 18 connecting these support chambers. A check valve 21 may be provided to a zone of the wall of the line segment 18, or of its orifice portion.

The delivery of the ambient air aspirated through the blower device 1 may be done via the receiving portion 2, without having to provide special line devices attached to the blower device 1 in a sealing manner. In an embodiment, the suspension device may be structured such that a structure that guides air is provided in the intake region of the blower device, through which structure a preferential flow course for carrying the air through the receiving portion 2 is formed. In an embodiment, the support chambers 11, 12 may be structured such that together they define an air delivery shaft or at least air guide walls.

The blower device 1 may be structured such that fastening portions of support chambers 9, 10, 11, 12, 13 may be attached to it, these portions being embodied as suitably complementary to it. In particular, sockets or insertion receptacles or cuffs may be provided into which corresponding elastomer insertion portions or folded-over portions of the support chambers 9, 10, 11, 12, 13 may be positioned.

FIG. 2 illustrates a suspension device for suspending a blower device of a CPAP device according to another embodiment of the invention. In this embodiment, the same comments as made above largely apply accordingly and similar components are indicated with similar reference numerals. In contrast to the embodiment described above, the embodiment of FIG. 2 includes a sound damping portion 30. As illustrated, the sound damping portion 30 is provided at the portion 3 on the compression side and is integral with the elastomer stub or tube 20. This sound damping portion 30, in the illustrated embodiment, forms an annular chamber 31 outlining a largely rectilinear diversion path portion. The geometry of the annular chamber, e.g., its diameter and axial length, may be defined empirically for the greatest possible sound damping effect. The inner wall of the annular chamber 31 may be designed with a surface geometry that supports the canceling out of sound especially well. The illustrated embodiment also may be suitable for sound damping on the intake side. Hence, it is possible to provide a corresponding elastomer stub for delivering air on the suction side as well.

The elastomer outlet stub 20, in the illustrated embodiment, may be coupled to the line segment 18, by way of which pressure is exerted on the support chambers 9, 10, 11, 12, 13.

On the basis of the construction characteristics shown here as examples, it becomes possible to accomplish the suspension of a blower device, intended for supplying a breathable gas, e.g., ambient air, in a way that is especially advantageous from the standpoint of acoustical properties of the apparatus. The bearing structure may be embodied as an integral structure, made from an elastomer material, e.g., silicone rubber. The suspension device 8 and the blower device 1 may be put together during a suitable assembly operation and inserted into a corresponding blower receiving chamber of a medical device, e.g., a CPAP device.

As an alternative to the line segment 18 on the elastomer portion 3 on the compression side, the impeller housing 32 may provide at some other point, located at an adequate pressure level and in particular at the supplying pressure level, a connection stub or connection port, by way of which pressure may be supplied to the support chambers 9, 10, 11, 12, 13.

A filter device may be provided in the region of the line segment 18, which largely prevents any contaminants from penetrating into the support chamber system. With respect to the embodiment shown in FIG. 2 of the sound damper device 31 on the compression side, elastic sound damping structures may be provided on the suction side as well, which prevent or at least reduce sound propagation, e.g., via the suction path, by suitable annular chambers or other kinds of chamber structures.

One possible mode of operation of the exemplary embodiments described above in conjunction with FIGS. 1*b* and 2 is as follows:

For supplying a breathing gas at a pressure level that is at least in some phases above the ambient pressure, a blower device 1 is provided, which includes an impeller 6 driven via a motor 4. The impeller 6 is received in a blower housing 32 (e.g., see FIG. 2). This blower housing 32 includes a diversion or pressure stub 33, which is inserted into an elastomer stub 20. During operation of the blower device 1, some of the air aspirated and supplied at a pressure level above the ambient pressure reaches the line segment 18, and by way of it reaches the support chambers 9, 10, 11, 12, 13. These support chambers 9, 10, 11, 12, 13 inflate as a consequence of the air pressure applied to their interior, and in the process they generate a bearing force that braces the blower device 1 in a receiving portion 2. Because of the low intrinsic mass and because of the particular acoustical properties of the suspension system designed in this way, a propagation of sound events generated by the blower device 1 into the wall forming the receiving portion 2, as well as into the rest of the device, is avoided. Depending on the particular breathing gas pressure required at the time, the blower device may be operated at different rotary speeds of the impeller. By means of the suspension system shown here, it becomes possible to adapt the rigidity of the suspension of the blower device to the instantaneous breathing gas pressure, so that the blower device 1 is suspended relatively softly, in a way that is advantageous for the sake of avoiding the propagation of structure-borne sound. By the coupling of the support chambers 9, 10, 11, 12, 13 to the region of the breathing gas tract system on the compression side, an adequate subjection of the support chambers to pressure is advantageously assured.

Aspects of the present invention are not limited to the exemplary embodiments described in detail here. For example, it is also possible, in addition to the support chambers 9, 10, 11, 12, 13 described here, to provide further suspension systems for additional suspension of the blower device. The support chambers 9, 10, 11, 12, 13 also may not necessarily be embodied as the balloon-like chambers shown here, but instead may be embodied as an annular expansion fold, concertina, or other kinds of air spring chambers.

Figure 3:
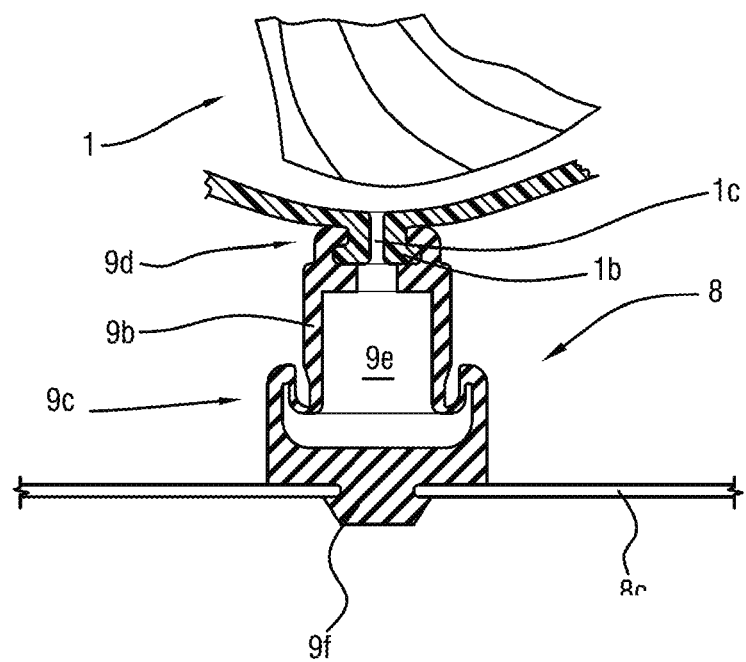
FIG. 3 is a cross-sectional view of a blower suspension according to another embodiment of the invention, using an air spring structure.

FIG. 3 illustrates a suspension device 8 for suspending a blower device 1 according to another embodiment of the present invention. As illustrated, the suspension device 8 includes an elastic support chamber 9b, which includes an annular expansion fold portion 9c. In the illustrated embodiment, the support chamber 9b is coupled to the blower device 1 via a fastening portion 9d. The blower device 1 includes a fastening plug portion 1b, which may be structured to engage the fastening portion 9d of the support chamber 9b. A pressure conduit 1c extends in the region of the fastening portion 1b, and through it, an inner chamber 9e provided in the support chamber 9b is acted upon by a pressure that is raised relative to the ambient pressure. The suspension device 8 is structured to provide, regardless of the pressure prevailing in the chamber 9e, an adequate suspension action. To that end, the suspension device is coupled not only to the blower device 1 but also to a housing portion 8c, through a fixation plug structure 9f integrally formed with the support chamber 9b.

Figure 4:
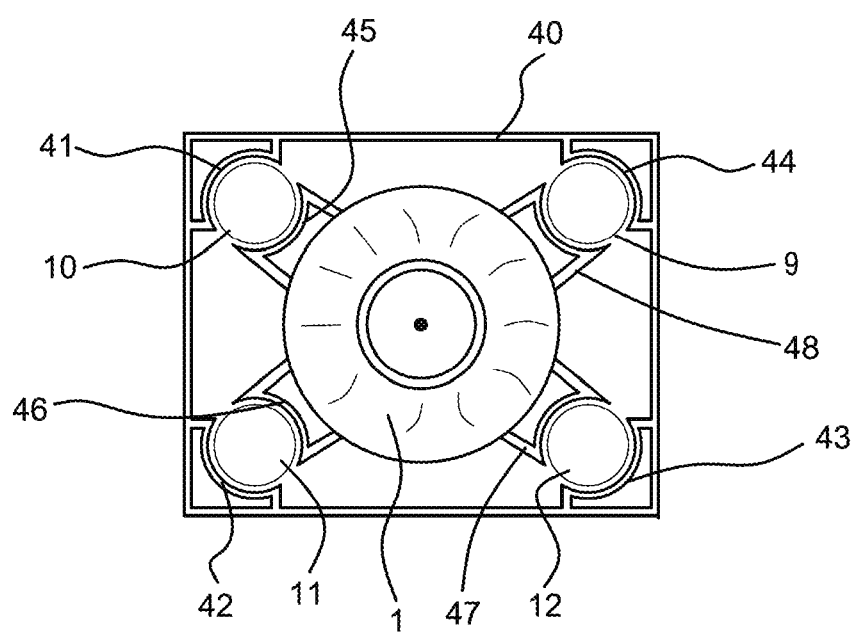
FIG. 4 is a sketch that illustrates a structure for supporting of a blower device in a receiving portion according to another embodiment of the invention, using air spring elements.

FIG. 4 illustrates a structure that defines a receiving portion or receiving housing 40 according to an embodiment of the present invention. As illustrated, retaining devices 41, 42, 43, 44 are provided in the receiving housing 40. The retaining devices 41, 42, 43, 44 are structured to retain the support chambers 9, 10, 11, 12 functioning as a suspension device in a defined way. The support chambers 9, 10, 11, 12 are in turn also seated in contact portions 45, 46, 47, 48 that are provided on the blower device 1. The support chambers 9, 10, 11, 12 may be structured in such a way that they are embodied as permanently sealed-off structures, and then no further connection to an additional pressure source may be made.

FIG. 5 illustrates a support chamber device 9 according to an embodiment of the present invention. The support chamber device 9 includes a support chamber interior 9e, which is at a defined pressure, and a stop structure 50, by which a defined minimum support effect is provided. In the illustrated embodiment, the stop structure 50 is structured as a peg that is integrally formed with the support chamber device 9. This peg may be seated in a pan portion 51 and in the process transmits a support force for minimum support of the blower device.

FIG. 6a illustrates a suspension device for a blower device including air chambers according to an embodiment of the invention. In the illustrated embodiment, the support chambers 9, 10, 11, 12 are structured as segmental chamber elements. These chamber elements may be attached from outside to a corresponding blower device and as a result may elastically, resiliently support the blower device in a receiving housing (not shown here). The support chambers 9, 10, 11, 12 may be provided with line elements, through which the support chambers 9, 10, 11, 12 may be connected with one another and optionally may be connected to the compression side of the blower device.

FIG. 6b shows the installed state of the support chambers 9 (10, 11, 12) inside a housing element 73. These support chambers are attached laterally to the blower device 1 and support it radially and axially.

FIG. 7 illustrates a blower device 1; on the intake side, the blower device 1 is coupled via an elastomer structure 70 to a through portion 71 according to an embodiment of the present invention. The through portion 71 makes an inflow of air to the blower device 1 possible and may be structured as a circular or polygonally contoured opening in a wall 72. The wall 72 may form part of a boxlike housing element 73, which receives the blower device 1 in encapsulated and vibration-insulated fashion. A further elastomer stub 74 may be provided in the inner region of the housing element 73. Stub 74 makes a connection on the compression side of the blower device 1 possible and also makes it possible to extend the line system on the compression side out of the housing element 73.

In the interior of the housing element 73, an air chamber device 75 is provided, which provides an air-cushioned suspension of the blower device 1. Further suspension structures, e.g., air spring devices, may be provided inside the housing element 73, which provide an elastic or resilient suspension of the blower device 1 in a way that is acoustically largely decoupled from the housing element 73.

In an embodiment, the air chamber device 75 may be structured as an axially resilient elastomer hose wrapped around the intake region of the blower device. The elastomer hose may form an integral component of the elastomer structure 70.

Figure 8:
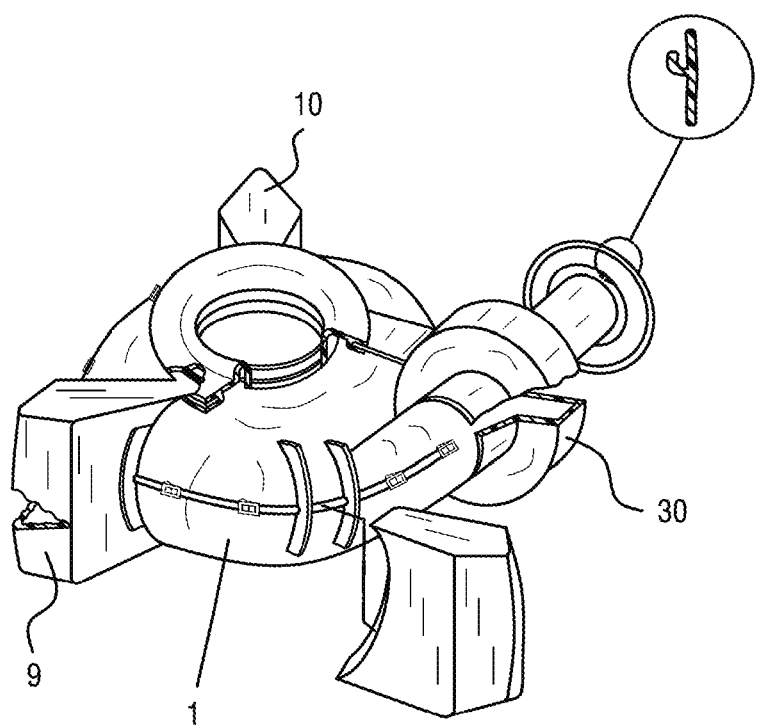
FIG. 8 is a sketch that illustrates an elastomer structure for elastic suspension of a blower device in a receiving portion according to an embodiment of the present invention.

FIG. 8 illustrates a blower device 1 that can be resiliently supported via elastomer structures in a receiving housing (not shown in FIG. 8) to isolate the blower device 1 in order to reduce transmission of noise and vibration. These elastomer structures may include the segmental chambers 9, 10 (also shown in FIG. 6a) and the elastic structure 30 arranged at the blower outlet. The elastic structure 30 may optionally be configured to further provide sound damping (e.g., functions as a muffler). In other embodiments, where multiple elastomer structures are incorporated into the blower outlet, all such structures may be pressure tight. Pressurization of the elastomer structures advantageously makes them more rigid, allowing them to better support the blower device 1.

Figure 9:
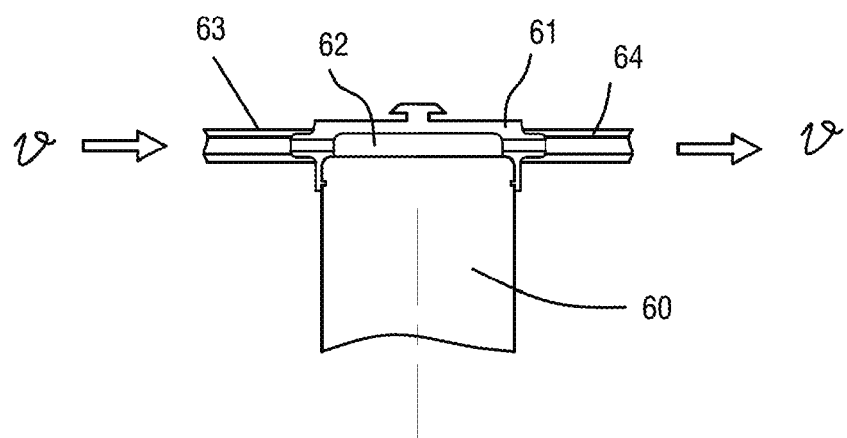
FIG. 9 is a sketch that illustrates an elastomer cooling chamber attached in a sealing fashion to a motor according to an embodiment of the present invention.

FIG. 9 illustrates an outer region of a blower motor 60 according to an embodiment of the present invention. A bell-shaped element 61, made of an elastomer material, may be slipped onto a rear wall region of the blower motor 60, This element 61, together with the outer wall of the motor 60, forms a cooling chamber 62. This cooling chamber 62 may be subjected, via a line device 63, to air diverted from the region of the applicable blower device on the compression side. The air delivered to the cooling chamber 62 and warmed in the cooling chamber maybe carried away to the outside via a further line device 64, for dissipating the heat released by the motor 60, without this air reaching the aspirated breathing air. It is also possible via the element 61 to accomplish an elastically resilient support of the motor 60, or of the blower device 1 equipped with this motor.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A CPAP apparatus for supplying a breathing gas at a pressure level that at least in some phases is above ambient pressure to a patient for therapy, the CPAP apparatus comprising:
    a blower device including an electric motor, an impeller driven by the electric motor, and a blower housing to receive the electric motor and the impeller, the blower device configured to generate a supply of pressurized gas;
    a housing element forming a blower receiving chamber; and
    an air spring system configured and arranged to elastically and resiliently support the blower device within the blower receiving chamber of the housing element,
    wherein the air spring system includes a plurality of elastic support chambers, each of the plurality of elastic support chambers including an expansion fold portion that allows relative movement between the blower device and the housing element.

2. The CPAP apparatus according to claim 1, wherein the expansion fold portion comprises a fold or concertina.

3. The CPAP apparatus according to claim 1, wherein each of the plurality of elastic support chambers includes an inner chamber pressurized by pressurized gas provided by the blower device.

4. The CPAP apparatus according to claim 3, wherein the blower device includes fastening plug portions structured to interlock with a respective fastening portion provided to each of the plurality of elastic support chambers, each of the fastening plug portions including a pressure conduit that allows pressurized gas from the blower device to be communicated with the inner chamber.

5. The CPAP apparatus according to claim 3, wherein each of the plurality of elastic support chambers provides suspension action regardless of pressure within the inner chamber.

6. The CPAP apparatus according to claim 3, wherein suspension rigidity provided by each of the plurality of elastic support chambers is variable as a function of the pressurized gas from the blower device.

7. The CPAP apparatus according to claim 3, wherein each of the plurality of elastic support chambers includes an inner chamber at a defined pressure.

8. The CPAP apparatus according to claim 7, wherein each of the plurality of elastic support chambers includes a stop structure configured to provide minimum support of the blower device.

9. The CPAP apparatus according to claim 1, wherein the air spring system forms a cassette-like receiving portion configured and arranged to receive the blower device within in a lateral direction.

10. The CPAP apparatus according to claim 1, wherein the housing element includes retaining devices configured and arranged to retain respective elastic support chambers of the air spring system.

11. The CPAP apparatus according to claim 1, wherein each of the plurality of elastic support chambers includes a first fastening portion coupled to the housing element and a second fastening portion coupled to the blower device.

12. The CPAP apparatus according to claim 11, wherein the expansion fold portion is provided between the first and second fastening portions to allows relative movement between the first and second fastening portions.

* * * * *

UNITED STATES PATENT AND TRADEMARK OFFICE
CERTIFICATE OF CORRECTION

PATENT NO. : 10,946,149 B2
APPLICATION NO. : 15/970189
DATED : March 16, 2021
INVENTOR(S) : Heidmann et al.

Page 1 of 1

It is certified that error appears in the above-identified patent and that said Letters Patent is hereby corrected as shown below:

In the Claims

Column 10, In Claim 9, Line 3, delete "within"; and

Column 10, In Claim 12, Line 3, delete "allows" and insert --allow--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*